US010271743B2

(12) United States Patent
Collins et al.

(10) Patent No.: US 10,271,743 B2
(45) Date of Patent: *Apr. 30, 2019

(54) SYSTEM FOR FACILITATING MEASUREMENT OF A PERSON'S BLOOD PRESSURE AND METHOD OF TAKING A BLOOD PRESSURE MEASUREMENT USING THE SYSTEM

(71) Applicant: HIGI SH LLC, Chicago, IL (US)

(72) Inventors: John R. Collins, Monrovia, CA (US); Jeffrey D. Flammer, Scottsdale, AZ (US)

(73) Assignee: Higi SH LLC, Chicago, IL (US)

( * ) Notice: Subject to any disclaimer, the term of this patent is extended or adjusted under 35 U.S.C. 154(b) by 846 days.

This patent is subject to a terminal disclaimer.

(21) Appl. No.: 14/287,308

(22) Filed: May 27, 2014

(65) Prior Publication Data

US 2015/0342474 A1   Dec. 3, 2015

(51) Int. Cl.
*A61B 5/02*        (2006.01)
*A61B 5/022*       (2006.01)
*A61B 5/00*        (2006.01)

(52) U.S. Cl.
CPC .......... *A61B 5/02233* (2013.01); *A61B 5/702* (2013.01); *A61B 5/6888* (2013.01)

(58) Field of Classification Search
CPC . A61B 5/02233; A61B 5/702; A61B 5/02141; A61B 5/6888; A61B 5/022
See application file for complete search history.

(56) References Cited

U.S. PATENT DOCUMENTS

| | | | | |
|---|---|---|---|---|
| 3,124,328 A | * | 3/1964 | Kortsch | A47C 1/03 248/118 |
| 6,428,124 B1 | * | 8/2002 | Bluth | A61B 5/0002 177/245 |
| 7,445,600 B1 | * | 11/2008 | Carr | A61B 5/0059 600/300 |
| 2008/0146950 A1 | * | 6/2008 | Fumuro | A61B 5/02233 600/499 |
| 2009/0216142 A1 | * | 8/2009 | Stelzer | A61B 5/04085 600/509 |
| 2011/0300994 A1 | * | 12/2011 | Verkaaik | A61H 1/0274 482/51 |
| 2013/0334851 A1 | * | 12/2013 | Hoell | A47C 3/18 297/217.2 |
| 2014/0187987 A1 | * | 7/2014 | Fraden | A61B 5/02233 600/499 |
| 2014/0350418 A1 | * | 11/2014 | Knopfel | A61B 5/02141 600/490 |

* cited by examiner

*Primary Examiner* — Eric J Messersmith
(74) *Attorney, Agent, or Firm* — Zarley Law Firm, P.L.C.

(57) ABSTRACT

A system for facilitating measurement of a person's blood pressure. The system has a cuff that is configured to: a) be operatively situated in relationship to a person's arm; and b) strategically exert pressure on the person's arm to controllably restrict blood flow therein. An arm positioning assembly is configured to be operatively engaged by a hand on the person's arm to consistently place the person's arm in relationship to the cuff with the cuff operatively situated in relationship to the person's arm as a blood pressure measurement is taken.

9 Claims, 10 Drawing Sheets

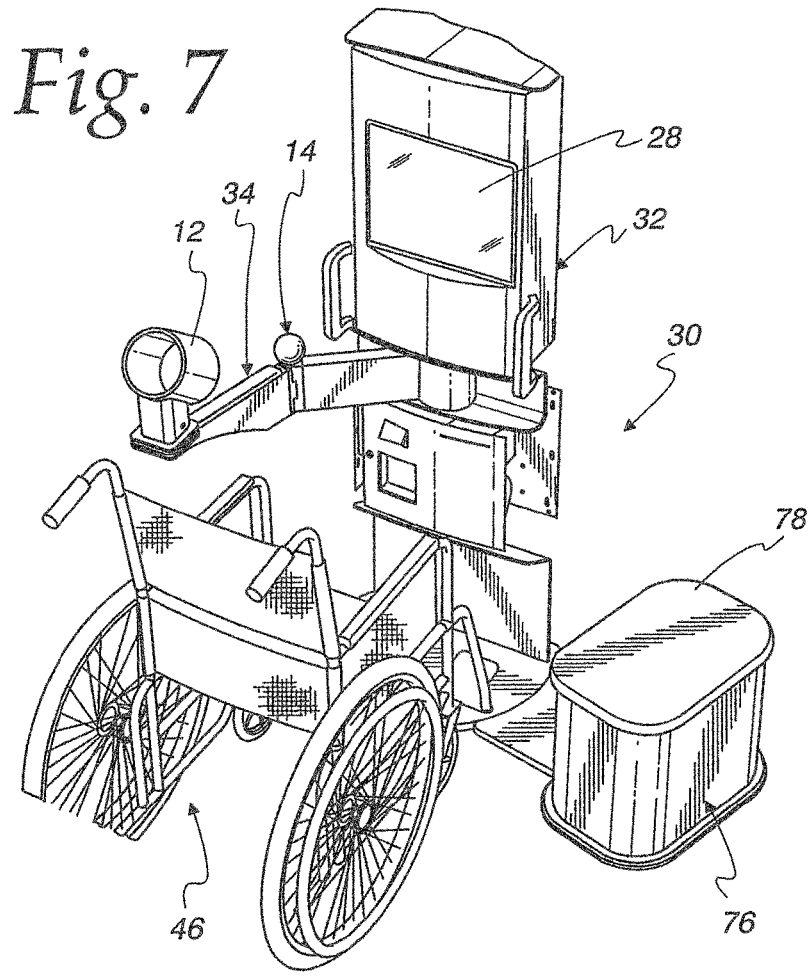
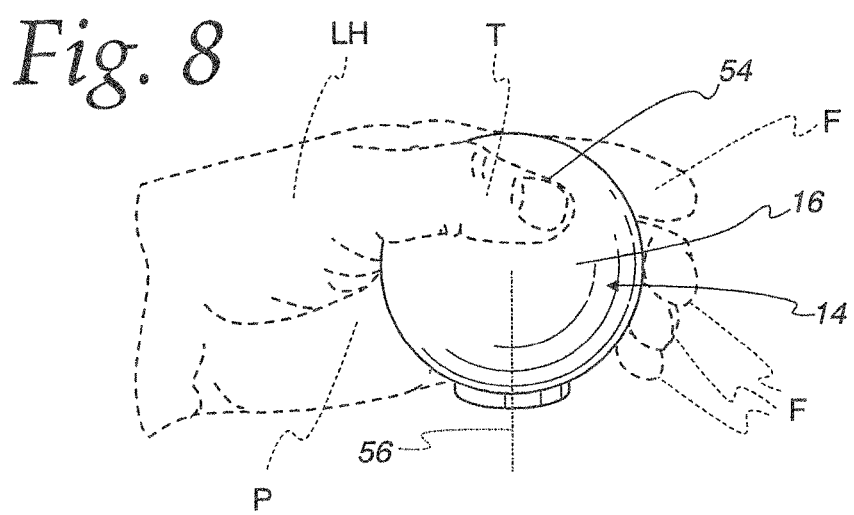

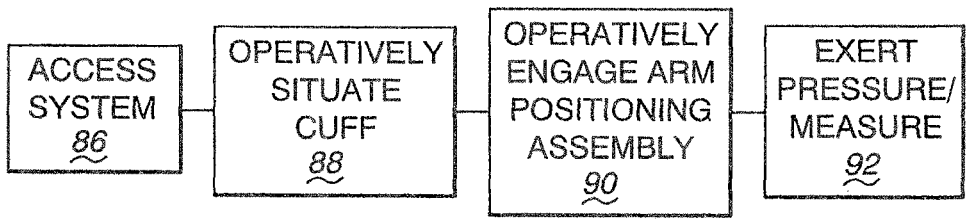
Fig. 15
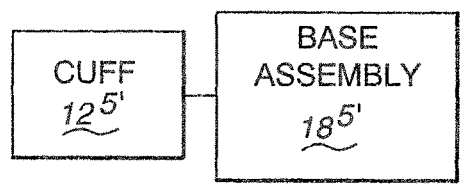
Fig. 16
Fig. 17
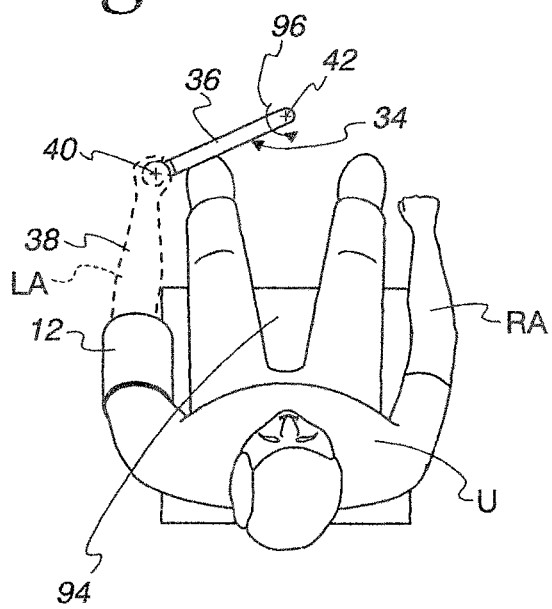
Fig. 18
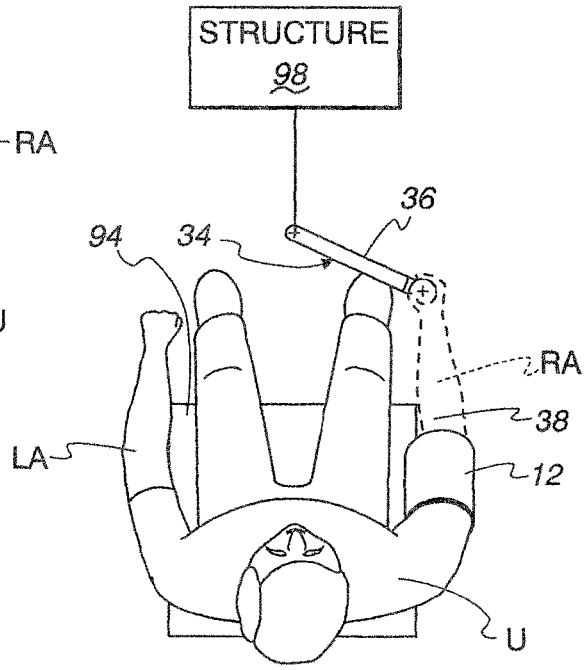

SYSTEM FOR FACILITATING MEASUREMENT OF A PERSON'S BLOOD PRESSURE AND METHOD OF TAKING A BLOOD PRESSURE MEASUREMENT USING THE SYSTEM

BACKGROUND OF THE INVENTION

Field of the Invention

This invention relates to blood pressure measurement and, more particularly, to a system for taking blood pressure measurements utilizing a cuff that extends around a person's limb.

Background Art

As the emphasis on improving individual health has increased worldwide, self-monitoring of body state has become more prevalent. Leading the way in this regard is blood pressure monitoring. For this purpose, many in-home systems are currently available for people to check their own blood pressure. Many businesses also provide kiosks at which blood pressure measuring equipment is provided.

Many of the existing systems utilize a blood pressure cuff with a housing that surrounds an individual's limb, such as the arm. The arm is directed into the cuff so that the cuff surrounds the upper arm region. The cuffs commonly have an inflatable bladder through which pressure can be strategically exerted on the person's arm to controllably restrict blood flow. A manometer is typically used to determine at which pressure blood flow starts and is unimpeded. Through conventional components, the developed data is converted to blood pressure readings.

In designing blood pressure monitors for use as in public places such as on kiosks, a number of different design challenges arise.

One overriding design objective is that equipment should be configured and operable so that the user is comfortably situated and can readily carry out the steps necessary to obtain a reading. Blood pressure readings may be skewed in the event that the person is not comfortably situated or becomes agitated during the process of preparing for, or taking, readings.

Further, kiosks must be configured to accommodate persons with disabilities. Thus, wheelchair access is required while at the same time accommodating those without wheelchairs. Equipment that has a fixed configuration has limited versatility and may result in awkward situation of some or all of the users of the blood pressure measuring equipment.

One often overlooked consideration in all types of blood pressure measuring equipment is that consistent readings require a consistent placement of the cuff on a user's arm. Blood pressure may vary significantly if the cuff takes measurements at different lengthwise locations on an individual's arm. For the most part, individuals are left on their own to determine the optimal location for placement of the cuff and how to repeatedly place the cuff at substantially the same location for successive measurements.

At this stage, blood monitoring equipment has evolved to the point that there is an expectation of accurate readings. This is true for systems that are designed for use at home and those that are available in public places. Consequently, one can anticipate that if the products that they offer are not accurate, those interested in purchase or use will be limited.

The industry continues to seek designs for blood pressure measuring equipment, as on kiosks, that is convenient to use, will be versatile in terms of accommodating different body types, and will take accurate measurements.

SUMMARY OF THE INVENTION

In one form, the invention is directed to a system for facilitating measurement of a person's blood pressure. The system has a cuff that is configured to: a) be operatively situated in relationship to a person's arm; and b) strategically exert pressure on the person's arm to controllably restrict blood flow therein. An arm positioning assembly is configured to be operatively engaged by a hand on the person's arm to consistently place the person's arm in relationship to the cuff with the cuff operatively situated in relationship to the person's arm as a blood pressure measurement is taken.

In one form, the arm positioning assembly is a component configured to be grasped in the person's hand.

In one form, the component has a rounded convex surface that conforms generally to the person's palm and fingers with the person's hand in a cupped configuration.

In one form, the component is at a fixed distance from the cuff.

In one form, the system is configured so that the fixed distance can be selectively changed.

In one form, the cuff has a generally cylindrical housing to surround a part of the person's arm with the cuff operatively situated. The housing has a central axis. The housing is supported on a base assembly with the cuff and base assembly configured so that the cuff housing can be selectively repositioned to change a relationship of the central axis of the housing to a part of the base assembly.

In one form, the cuff and arm positioning assembly are supported on a base assembly.

In one form, the base assembly has an elongate, cantilevered arm.

In one form, the system is provided in combination with a support frame assembly and a support surface upon which the person can sit to take a blood pressure reading using the system. The base assembly is connected to the frame assembly.

In one form, the system is provided in combination with components to measure the person's blood pressure with the cuff operatively situated and pressure exerted on the person's arm through the cuff.

In one form, the system is further provided in combination with a monitor on the support frame assembly through which blood pressure measurements taken through the components are displayed.

In one form, the base assembly has an elongate arm cantilever mounted to the support frame assembly.

In one form, the elongate arm has an articulated construction including at least first and second relatively movable parts.

In one form, the first and second parts are movable relative to each other around a first axis. The arm positioning assembly has a component configured to be grasped in the person's hand. The component is at or adjacent to the first axis.

In one form, the first axis is substantially vertically oriented. The elongate arm is connected to the support frame assembly for movement relative thereto around a second axis that is substantially parallel to the first axis.

In one form, the support surface is defined by a wheelchair.

In one form, the support surface is defined on a seating component. The seating component is connected to the support frame assembly so as to be movable selectively relative to the support frame assembly between: a) an active position; and b) a stored position. The seating component in the stored position is situated so that a person in a wheelchair can move into a position in which the person while seated in the wheelchair can operatively situate the cuff with respect to his/her arm.

In one form, the invention is directed to a method of taking a person's blood pressure measurement. The method includes the steps of: accessing a system for facilitating measurement of the person's blood pressure as described above, together with components to measure the person's blood pressure; operatively situating the cuff on one of the user's arms; with the user's hand on the one arm, operatively engaging the arm positioning assembly to establish a resting position for the one of the user's arms; with the user's hand in the resting position, causing: a) the cuff to exert pressure on the user's one arm; and b) the components to measure the person's blood pressure.

In one form, the step of operatively engaging the arm positioning assembly involves grasping a part of the arm positioning assembly.

In one form, the steps of causing: a) the cuff to exert pressure on the person's arm; and b) the components to measure the user's blood pressure are carried out while the user continues to grasp the part of the arm positioning assembly.

BRIEF DESCRIPTION OF THE DRAWINGS

FIG. 7 is a view as in FIGS. 3-6 from yet another different perspective;

FIG. 8 is an enlarged, fragmentary view of a component of an arm positioning assembly, on the system in FIG. 1 and on the kiosk in FIGS. 3-7, that is grasped by the hand on an arm of a user on which the cuff is operatively situated;

FIG. 15 is a flow diagram representation of a method of taking a blood pressure measurement according to the present invention;

FIG. 16 is a schematic representation of a modified form of system, according to the invention, for facilitating measurement of a person's blood pressure;

FIG. 17 is a plan view of the inventive system, as shown in FIGS. 1-16, and with an elongate arm, that is part of the base assembly, positioned to take a blood pressure measurement using the left arm of the person situated in a measurement taking position;

FIG. 18 is a view as in FIG. 17 wherein the elongate arm has been reconfigured to allow measurement of the person's blood pressure through the person's right arm with the person situated in the same measurement taking position;

DETAILED DESCRIPTION OF THE PREFERRED EMBODIMENT

Figure 1:
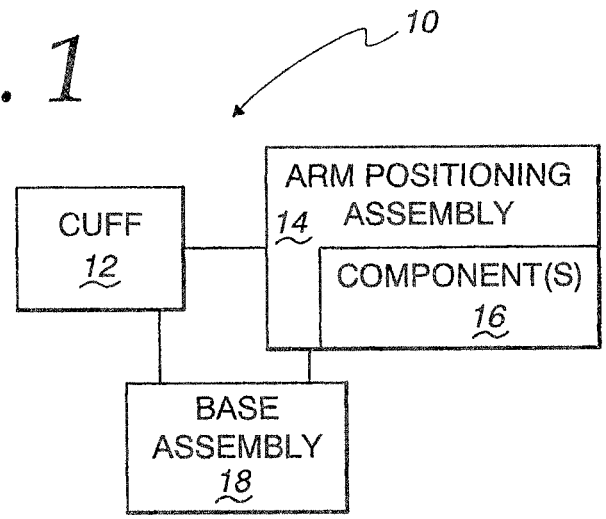
FIG. 1 is a schematic representation of a system for facilitating measurement of a person's blood pressure, according to the present invention.

In FIG. 1, a system for facilitating measurement of a person's blood pressure, according to the present invention, is shown schematically at 10. The system 10 consists of a cuff 12 that is configured to: a) be operatively situated in relationship to a person's arm; and b) strategically exert pressure on the person's arm to controllably restrict blood flow therein to allow the person's blood pressure to be conventionally measured. The system further includes an arm positioning assembly 14, configured to be operatively engaged by a hand on the person's arm, to consistently place the person's arm in relationship to the cuff 12, with the cuff 12 operatively situated in relationship to the person's arm as a blood pressure measurement is taken. The arm positioning assembly 14 includes at least one component 16 that is engaged by a person's hand to facilitate the consistent placement of the arm relative to the cuff 12.

The cuff 12 and arm positioning assembly 14 are supported upon a base assembly 18. The base assembly 18 may be a single component or separate components.

In FIG. 1, as in other Figures described hereinbelow, the schematic showing of components is intended to encompass the specific components described herein in the preferred embodiments, and virtually an unlimited number of variations of these components and their interactions, as would be apparent to one skilled in the art with the present teachings in hand. The schematic showing is intended to encompass all such variations.

In FIG. 1, the generic showing of the component 16 is intended to broadly encompass virtually any type of component that the user's hand can abut to or grasp to allow a user to consistently achieve the same relationship between the arm and the cuff 12, with the cuff 12 operatively situated. The component 16 might be an abutting wall to which the user's fingertip(s), clenched fist, etc. abuts. Alternatively, and more preferably, the component 12 is graspable as in the various preferred embodiments described hereinbelow.

It is not necessary to understand the details of the components and instrumentation utilized to take an actual blood pressure reading to fully understand the present invention. Those basic components can be selected from the wide range of the same that are currently known and available, or become available.

Figure 2:
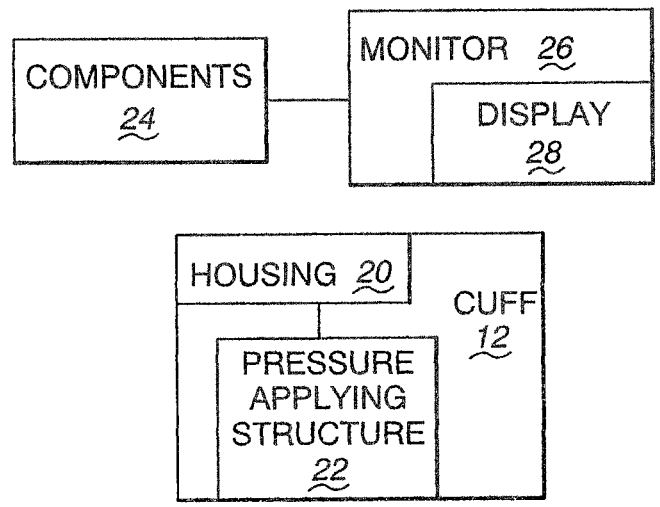
FIG. 2 is a schematic representation of the system in FIG. 1 and additional components used to measure blood pressure and display measured blood pressure values.
Figure 3:
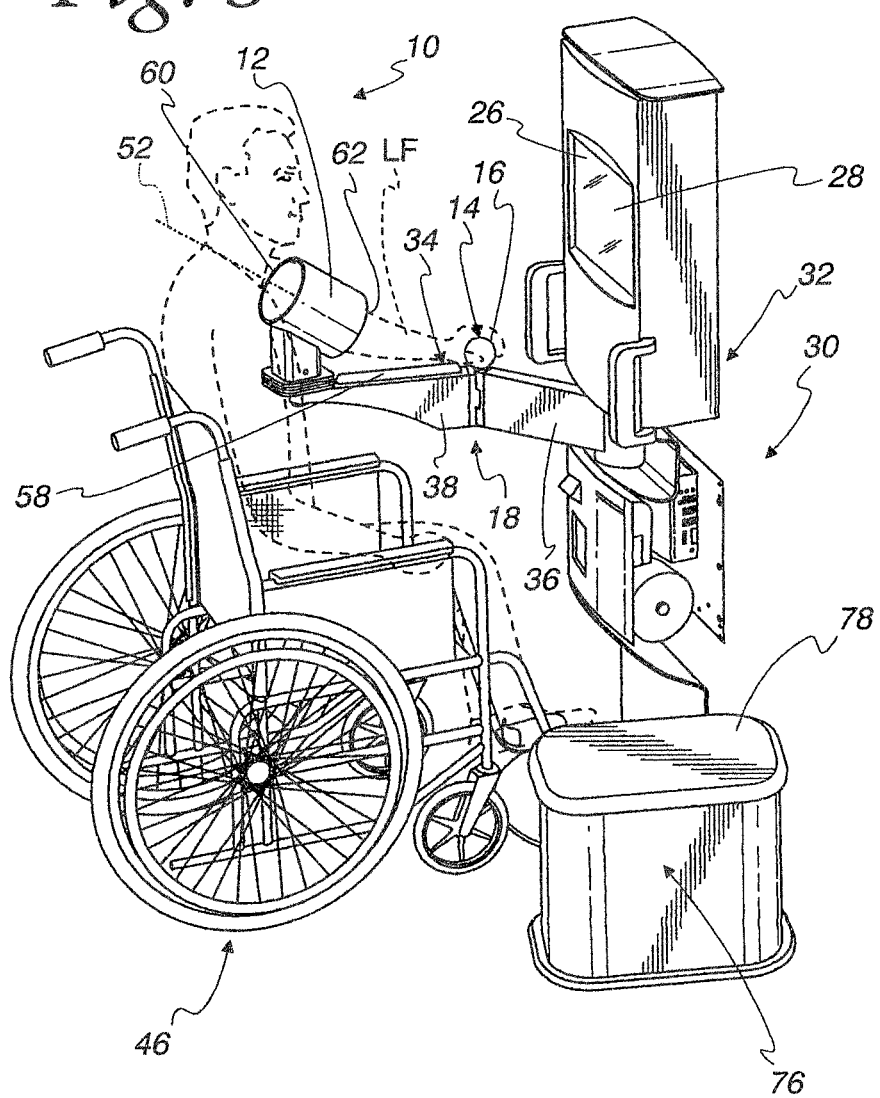
FIG. 3 is a perspective view of a kiosk incorporating one form of the system in FIG. 1 and the additional components in FIG. 2 and showing a user in a wheelchair and his/her left arm positioned to take a blood pressure reading.
Figure 4:
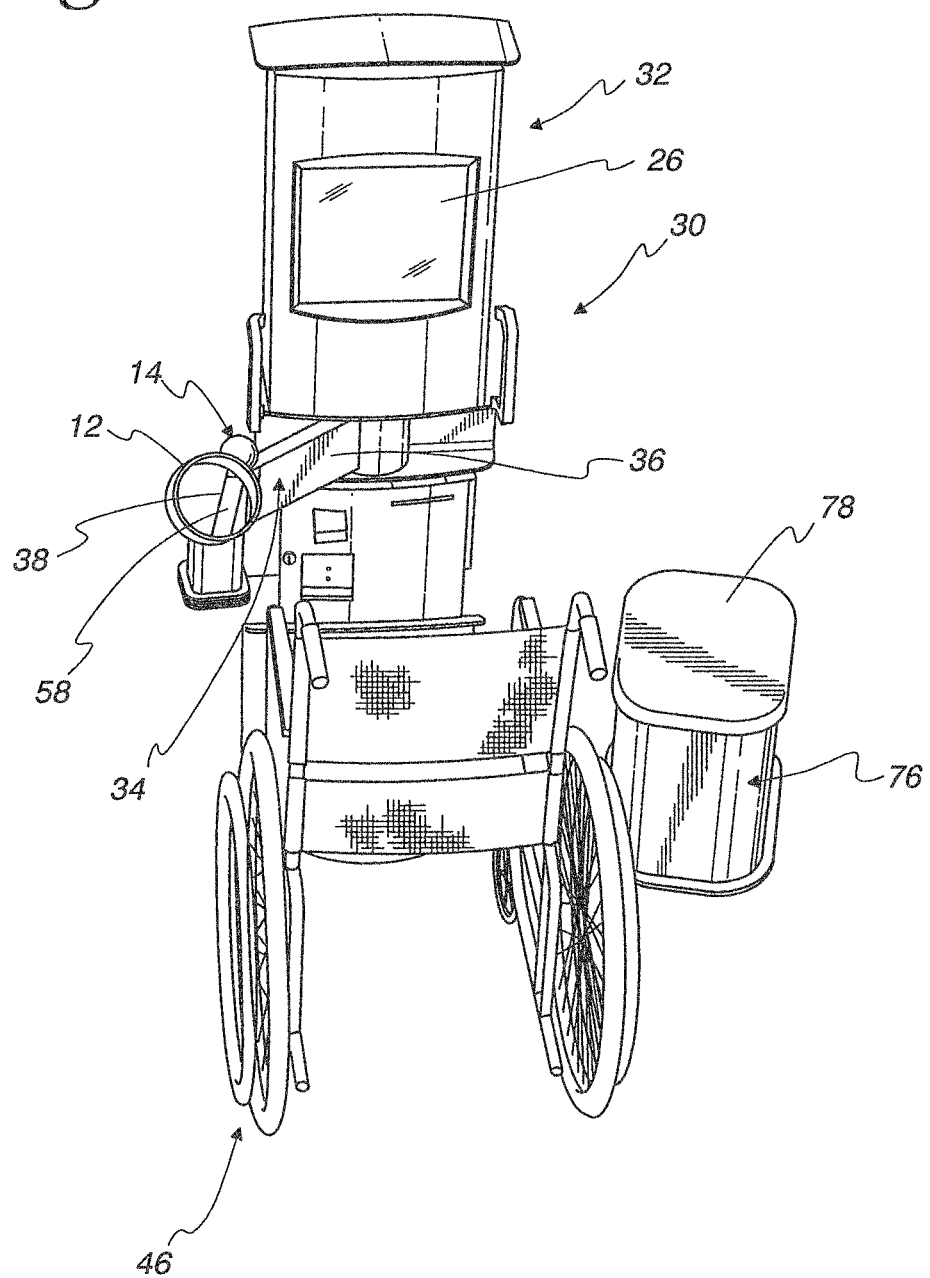
FIG. 4 is a view of the components in FIG. 3 from a different perspective.
Figure 5:
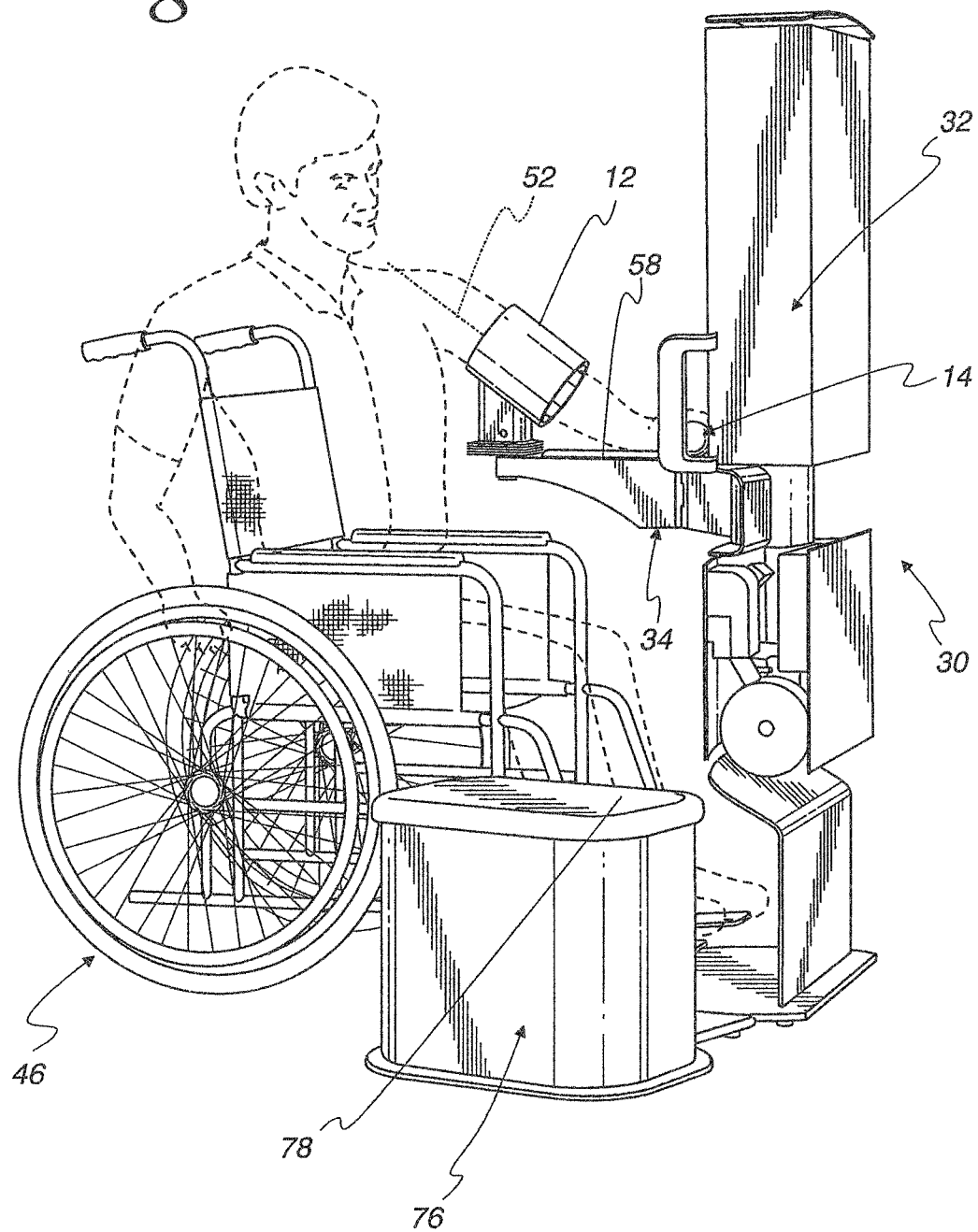
FIG. 5 is a view as in FIGS. 3 and 4 from another different perspective.
Figure 6:
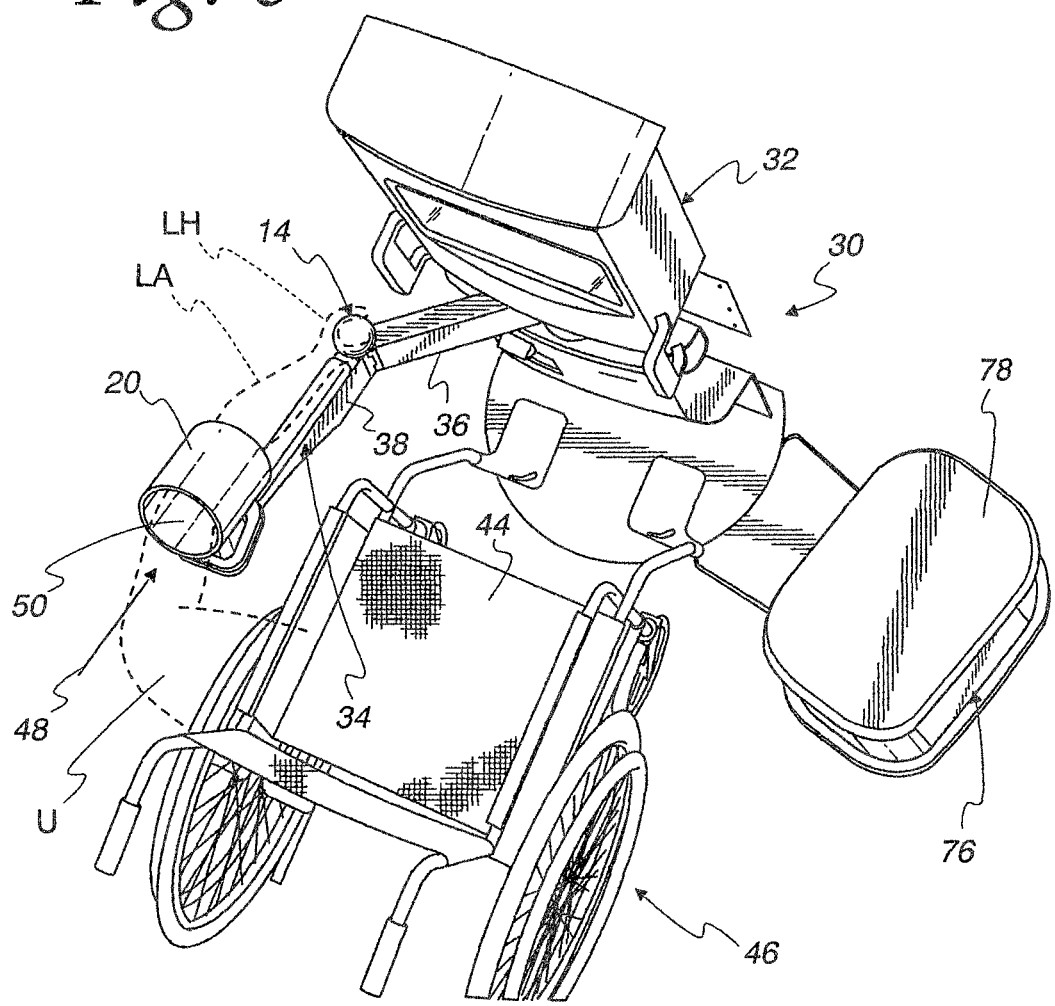
FIG. 6 is a view as in FIGS. 3-5 from a still further different perspective.
Figure 9:
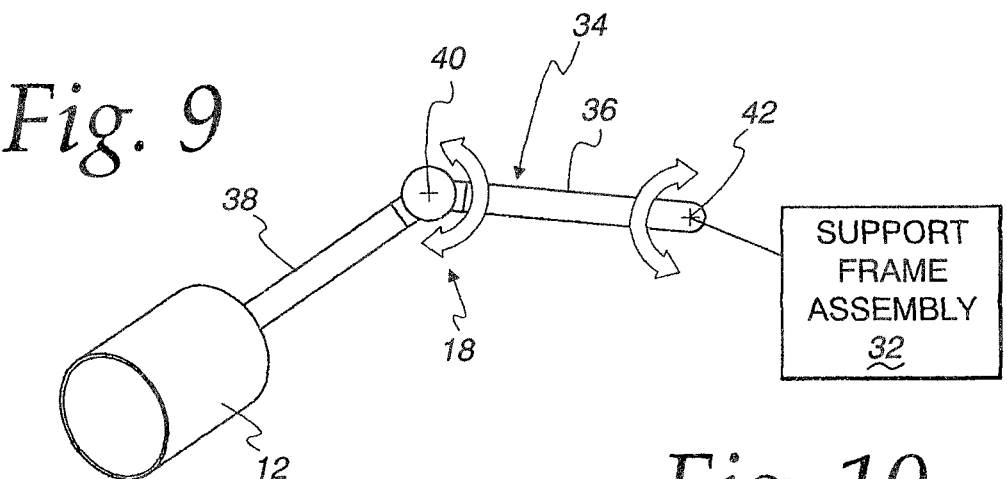
FIG. 9 is a partially schematic representation of separate articulating parts that make up a base assembly that supports the cuff and the arm repositioning assembly.
Figure 10:
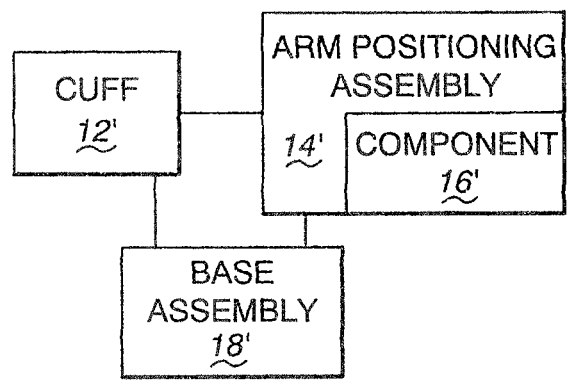
FIG. 10 is a schematic representation of a modified form of system, as shown in FIG. 1.

As shown schematically in FIG. 2, the cuff 12 has a housing 20 that extends around the wearer's arm. A pressure applying structure 22 resides within the housing 20 and may be in the form of a bladder which is either manually or automatically filled to apply a peripheral pressure on the user's arm to impede blood flow therein.

Components 24 are shown in FIG. 2 and encompass manometers and other components used to sense the blood pressure with the pressure applying structure exerting different pressures and with that pressure relieved. The components 24 convey signals to a monitor 26 that has a display 28 upon which blood pressure values can be viewed. The monitor 26 may include processing components or, alternatively, the processing can be done by one or more of the components 24.

Referring now to FIGS. 3-14 and 16-19, alternative and specific forms of the inventive system 10, as shown schematically in FIGS. 1 and 2, will be described. The system 10 is shown as part of a kiosk 30; however, it is not a requirement that the system 10 be part of a kiosk arrangement. For purposes of illustration, the kiosk 30 will be the exemplary environment for the system 10.

The kiosk 30 consists of a support frame assembly 32 which incorporates the aforementioned monitor 26 having the display 28 for electronically displaying the blood pressure readings.

In this embodiment, the base assembly 18 is in the form of an elongate, cantilevered arm 34. The arm 34 supports the cuff 12 at one location and the arm positioning assembly 14 at a location spaced from the cuff 12 between the cuff 12 and support frame assembly 32.

The elongate arm 34 has an articulated construction, including first and second relatively movable parts 36, 38, respectively. The parts 36, 38 are shown to be connected for relative movement in one manner, with it being understood that other mechanisms are contemplated that will allow controlled repositioning of the cuff 12 relative to the support frame assembly 32.

In this embodiment, the first and second parts 36, 38 are movable relative to each other around a first axis 40 that extends substantially vertically. The first part 36 of the elongate arm 34 is connected to the support frame assembly 32 for movement relative thereto around a second axis 42 that is substantially parallel to the first axis 40. Through this mechanism, the cuff 12 can be moved selectively towards and away from the support frame assembly 32 and simultaneously shifted additionally in a lateral direction while maintaining a desired orientation of the cuff 12 that facilitates direction of a user's arm therethrough.

The kiosk 30 is configured so that the user U can sit on a support surface while a blood pressure measurement is taken. In one form, the support surface 44 upon which the person sits in the measurement taking position is defined upon a wheelchair 46 that can be advanced into a ready position as shown in FIGS. 3-7. With the wheelchair 46 in the ready position, the user can advance the hand LH on his/her left arm LA in the direction of the arrow 48 in FIG. 6 through an opening 50 bounded by the housing 20. The opening 50 has a central axis 52 which is parallel to the advancing direction of the user's left arm that is effected to operatively situate the cuff 12 in relationship to the person's left arm LA. A preferred location for the cuff 12 is in the region above the user's elbow, whereby the left forearm LF projects from the cuff 12 towards the arm positioning assembly 14.

In this embodiment, the component 16 on the arm positioning assembly 14 has a rounded, convex surface 54 that conforms generally to the person's palm P, thumb T, and fingers F, with the person's left hand LH in a cupped configuration as shown in FIG. 8. The user's hand thus grasps the component 16 much in the same way as he/she would grasp a baseball, preparatory to a pitch. The particular diameter of the component 16 is not critical, as repetitive grasping of different sizes thereof would consistently place the hand at the same distance from the cuff 12. As a result, by directing the hand through the cuff opening 50 and grasping the component 16, the cuff 12 will consistently align at the same lengthwise location on the user's arm.

In this embodiment, the component 16 is shown as a substantially spherical element that has a vertical central axis 56 that is adjacent to, or coincident with, the first axis 40.

It should be understood that while a substantially raised spherical shape for the component 16 is shown, many other different shapes are contemplated. What is preferred is that, whatever the shape is, a user would naturally consistently effect grasping thereof, as an incident of which the user's arm in a resting position is repeatedly placed in the same relationship with the cuff 12 as successive measurements are taken.

The second arm part 38 has an upwardly facing surface 58 configurable in different shapes and against which a portion of the user's forearm region, and potentially the elbow, can be rested. By supporting the weight of the user's arm, the user can be comfortably resting as the measurement is being taken. The forearm region of the resting arm may alternatively be spaced above the surface 58, bridging between the cuff 12 and component 16.

The cuff 12 is shown fixedly mounted to the second part 38 so as to move as one piece therewith. In the fixed orientation, the axis 52 for the cuff opening 50 declines between a rear cuff edge 60 and a front cuff edge 62. This angle is chosen to nominally match the normal angle of a user's upper arm directed into the cuff 12 with the user seated in a measurement taking position at the kiosk 30 and the arm in a resting position.

In this embodiment, the distance between the cuff 12 and component 16 is fixed. In an alternative form of base assembly, as shown at 18' in FIG. 10, the distance between a cuff 12' and a component 16' on an arm positioning assembly 14' may be varied to accommodate different arm lengths of users. Through the base assembly 18', the distance between the cuff 12' and component 16' can be selectively changed and fixed using well known components and mechanisms.

Figure 11:
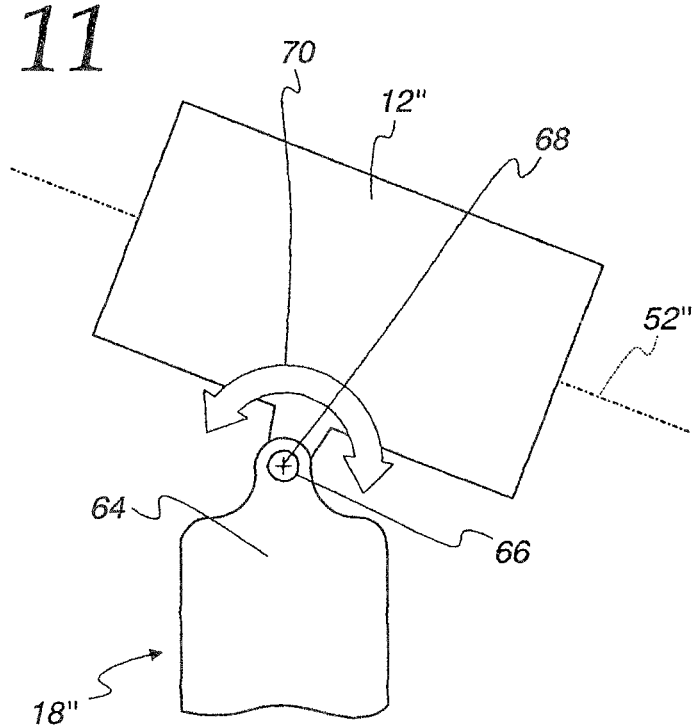
FIG. 11 is a fragmentary, side elevation view of a modified form of cuff and base assembly through which the cuff can be reoriented relative to the base assembly.

As shown in FIG. 11, a further modified form of base assembly at 18" may incorporate a part 64 that cooperates with a cuff 12" so as to allow the angular orientation of the cuff opening axis 52" to be changed. As one example, a pin 66 can be used to connect the cuff 12" and part 64 so that the cuff 12" is movable around a generally horizontal axis 68 defined by the pin 66, as indicated by the double-headed arrow 70.

Figure 12:
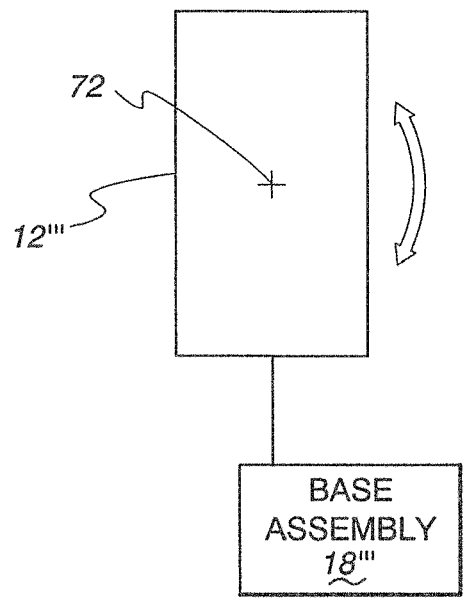
FIG. 12 is a partially schematic representation of a further modified form of cuff and cooperating base assembly that allow another dimension of movement of the cuff relative to the base assembly.

A still further modified form of base assembly 18' is shown in FIG. 12 through which the cuff 12" can be turned around a vertical axis 72 to further accommodate different body types and positioning.

Figure 13:
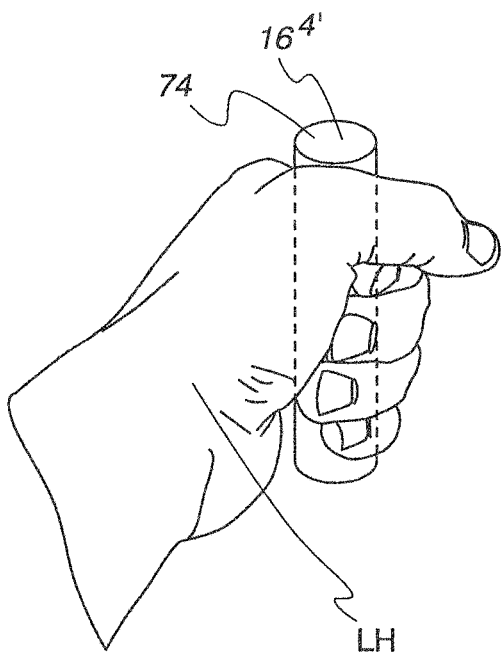
FIG. 13 is a perspective view of a modified form of component, corresponding to that in FIG. 8, making up an arm positioning assembly that can be grasped in a different manner by a user.

As a further modification, a graspable component 16⁴', as shown in FIG. 13, may be used in place of the graspable component 16. The graspable component 16⁴' is in the form of a cylindrical body 74 that can be horizontally situated, vertically situated, or angularly turned to a position therebetween to allow a user to grasp the body 74 generally as shown.

Figure 14:
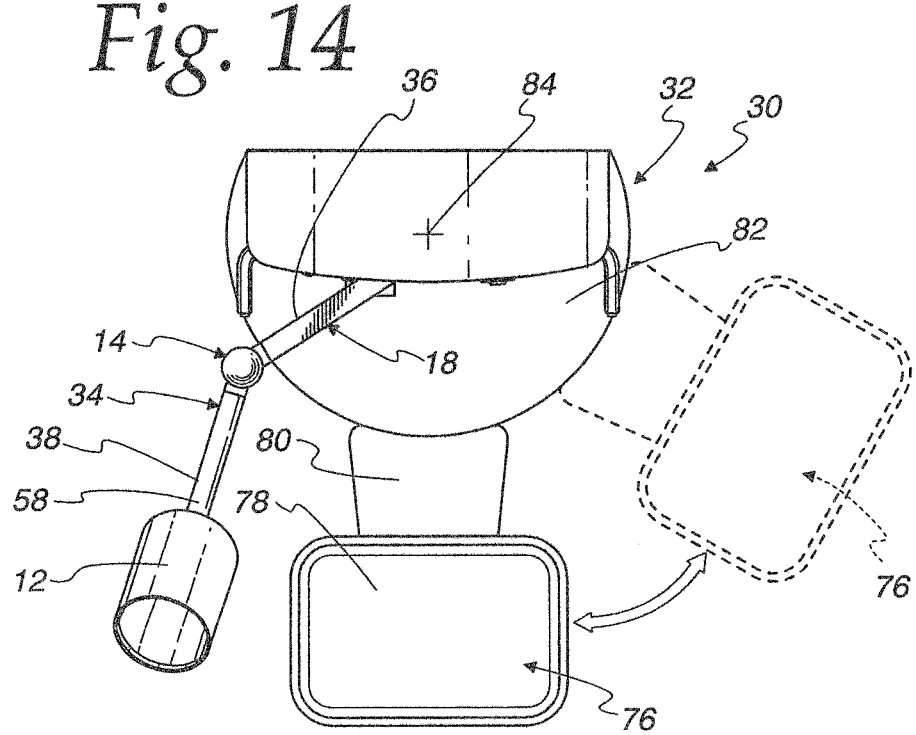
FIG. 14 is a view similar to that in FIG. 6 and with the wheelchair removed and a seating component for a user in two different positions.

Another feature of the kiosk 30 is the ability to place a seating component 76 with a support surface 78 selectively in an active position, as shown in solid lines in FIG. 14, and a stored position, as shown in dotted lines in FIG. 14 and in solid lines in FIGS. 3-7. The seating component 76 has a mounting arm 80 that connects to a plate 82 at the bottom of the support frame assembly 32. The plate 82 and support 80 have components thereon that cooperate so that the mounting arm 80 and associated seating component 76 turn about an axis 84 relative to the support frame assembly 32 in changing between the active and stored positions. The precise connection between the mounting arm 80 and plate 82 is not shown in any detail, as many different suitable connecting components might be incorporated to allow this interaction, or a similar interaction that permits controlled repositioning of the seating component 76.

With the seating component 76 in the active position, the support surface 78 thereon supports the user in a measurement taking position for convenient access to the cuff 12. With the seating component 76 in the stored position, a person in a wheel chair can move into the position shown in FIGS. 3-7, as described above, to allow the user to assume essentially the same measurement taking position.

Alternatively, the arm 34 could be situated at a height such that the user can stand while taking a measurement.

With the above structure, a method of taking a person's blood pressure measurement can be carried out, as shown in flow diagram form in FIG. 15.

As shown at block 86, the user accesses any form of the system, as described above.

As shown at block 88, the cuff is operatively situated on one of the user's arms.

As shown at block 90, the user operatively engages the hand on the arm within the cuff with the arm positioning assembly to establish a resting position for the user's arm.

As shown at block 92, with the user's hand in the resting position, the user causes: a) the cuff to exert pressure on the user's arm; and b) the components to measure the person's blood pressure.

The step of operatively engaging the arm positioning assembly may be simply abutting a part of the hand against the component or, more preferably, involves grasping that component.

In a preferred form of the method, the user continues to grasp the part of the arm positioning assembly as the cuff is exerting pressure and the components measure blood pressure.

Figure 19:
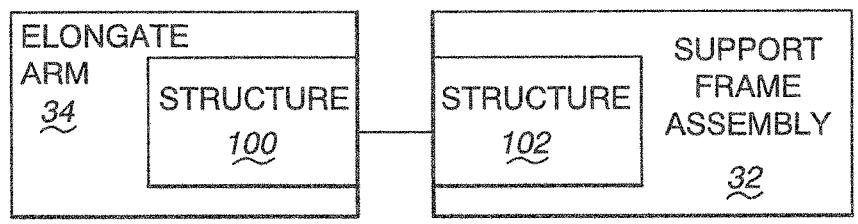
FIG. 19 is a schematic representation of structure for releasably and consistently maintaining the elongate arm and support frame assembly in the two different relationships, as shown in FIGS. 17 and 18.

Another aspect of the invention, in the form as described above, is shown generically in FIG. 16 and more specifically in FIGS. 17-19. The specific structure shown in these Figures is part of the embodiments described hereinabove, with it contemplated that the features shown in FIGS. 16-19 could incorporate any and all the components heretofore described.

In a generic sense, the inventive system 10⁵' in FIG. 16 has a cuff 12⁵' and base assembly 18⁵', corresponding generally to the cuff 12 and base assembly 18, and variations thereof, as described above. The generic showing is intended to encompass the specific structures described above and below, and other structure that may perform the described function using different components that may interact differently.

The cuff 12⁵' is configured to: a) be operatively situated in relationship to a person's arm; and b) strategically exert pressure on the person's arm to controllably restrict blood flow therein. The base assembly 18⁵' supports the cuff 12⁵'. The base assembly 18⁵' is configured to allow selective placement of the cuff 12⁵' in first and second different positions relative to a person with the person in a measurement taking position. The cuff 12⁵' in the first position is configured to be operatively situated in relationship to the person's left arm LA. The cuff 12⁵' in the second position therefor is configured to be operatively situated in relationship to the person's right arm RA, in the same manner as described above.

More specifically, with the components hereinabove described, the elongate arm 34 can be reconfigured from the FIG. 17 position into the FIG. 18 position therefor, thereby to change the cuff 12 between its first position in FIG. 17 and its second position in FIG. 18. The cuff 12 can be repositioned with the person/user U in substantially the same measurement taking position upon a support surface 94, which is intended to generically represent the support surface that may be defined by the wheelchair 46, the seating component 76, or a subjacent surface upon which the person might be standing when a blood pressure measurement is taken.

In effecting repositioning of the cuff 12, the first part 36 is pivoted about the axis 42 in the direction of the arrow 96 from the FIG. 17 position. At the same time, the parts 36, 38 pivot relative to each other around the first axis 40 to assume the configuration in FIG. 18. Each of the person's left and right arms LA, RA cooperates with the cuff 12 in substantially the same manner.

The elongate arm 34 cooperates with the other structures, including the support frame assembly 32, as described above. Alternatively, as shown in FIG. 18, the elongate arm 34 might cooperate with another type of structure, shown generically at 98 that permits reconfiguration of the elongate arm 34 relative to the person residing in a measurement taking position. Preferably, the measurement taking position for the user does not have to substantially change to allow measurements to be taken separately on left and right arms.

As shown in FIG. 19, structure 100, 102 may be provided separately on the elongate arm 34 and support frame assembly 32 that cooperates to consistently, but releasably, maintain the arm 34 in first and second positions, as shown in FIGS. 17 and 18, in which the cuff 12 is respectively maintained in its first and second positions.

Figure 20:
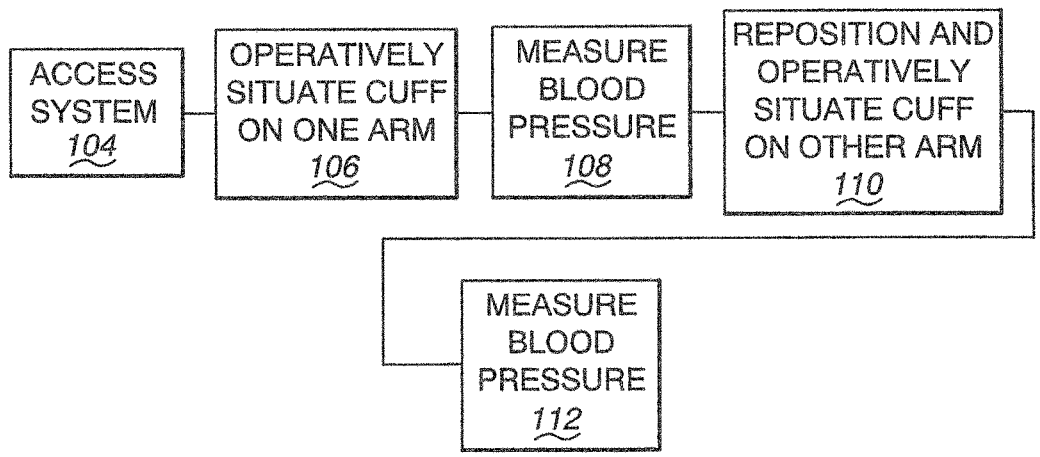
FIG. 20 is a flow diagram representation of a method of taking a person's blood pressure measurement according to the present invention.

With the system as described above, and as seen most clearly with reference to FIGS. 16-19, a method of taking a person's blood pressure measurement can be carried out as shown in flow diagram form in FIG. 20.

As shown at block 104, a system is accessed for facilitating measurement of the person's blood pressure, as described above, including components to measure the person's blood pressure.

As shown at block 106, the cuff is operatively situated on one of the user's arms with the user's one arm in a first resting position.

As shown at block 108, with the user's one arm in the first resting position, the cuff is caused to exert pressure on the user's one arm and the components are caused to measure the person's blood pressure through the person's one arm.

As shown at block 110, after measuring the person's blood pressure through the person's one arm, the cuff is repositioned and operatively situated on the other of the user's arms with the user's other arm in a second resting position.

As shown at block 112, with the user's other arm in the second resting position, the cuff is caused to exert pressure on the user's other arm and the components are caused to measure the person's blood pressure through the person's other arm.

The foregoing disclosure of specific embodiments is intended to be illustrative of the broad concepts comprehended by the invention.

What is claimed is:

1. A system for facilitating measurement of a person's blood pressure, comprising:
    a cuff having a housing and a pressure applying structure;
    a base assembly having an arm that supports the cuff wherein the arm has first and second parts that are moveable about a first axis and a second axis; and
    an arm positioning assembly adapted to conform to a person's palm, supported by the base assembly, and having a vertical central axis coincident with the first axis of the base assembly.

2. The system of claim 1 wherein the base assembly is pivotally connected to a support frame assembly.

3. The system of claim 2 wherein the support frame assembly is a kiosk having a monitor.

4. The system of claim 1 wherein the arm positioning assembly is spherical.

5. The system of claim 1 wherein the arm positioning assembly has a rounded convex surface adapted to conform to the person's palm, thumb, and fingers.

6. The system of claim 1 wherein the arm positioning assembly has a cylindrical body.

7. The system of claim 2 wherein the arm positioning assembly is between the cuff and the support frame assembly.

8. The system of claim 7 wherein a distance between the cuff and the arm positioning assembly is selectively changed through the base assembly.

9. A method of taking a person's blood pressure measurement, the method comprising the steps of:
    accessing a system for facilitating measurement of the person's blood pressure as in claim 1 together with components to measure the person's blood pressure;
    operatively situating the cuff on one of the user's arms;
    with the user's hand on the one arm, operatively engaging the arm positioning assembly by grasping a part of the arm positioning assembly to establish a resting position for the one of the user's arms;
    with the user's hand in the resting position, causing: a) the cuff to exert pressure on the user's one arm; and b) the components to measure the person's blood pressure are carried out while the user continues to grasp the part of the arm positioning assembly; and
    moving the cuff selectively towards and away from the support frame assembly by operatively engaging the elongate arm.

* * * * *